US00PP37590P2

(12) United States Plant Patent
Byrne et al.

(10) Patent No.: US PP37,590 P2
(45) Date of Patent: Aug. 18, 2026

(54) PEACH TREE NAMED 'TRH2E120LW'

(50) Latin Name: *Prunus persica.*
Varietal Denomination: TRH2E120LW

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,363

(22) Filed: Sep. 22, 2025

(51) Int. Cl.
*A01H 5/08* (2018.01)

(52) U.S. Cl.
USPC ..... Plt./195

(58) Field of Classification Search
USPC ..... Plt./156, 180, 194, 195
See application file for complete search history.

(56) References Cited

U.S. PATENT DOCUMENTS

PP28,360 P3 9/2017 Byrne et al.

OTHER PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.
Sherman and Lyrene. 1989. Flordaglo Peach. HortScience 24:396.
Byrne and Boonprakob. 2008. Thai Tiger™ Series of Low-chill Peaches for the Subtropics. HortScience 43(7):2226-2227.

*Primary Examiner* — Karen M Redden
(74) *Attorney, Agent, or Firm* — Dentons US LLP

(57) ABSTRACT

Disclosed is a new variety of *Prunus persica* named 'TRH2E120LW'. This new variety, which requires approximately 250 chilling units of dormancy, is considered to be a peach tree of early mid-season maturity, which produces white-fleshed, subacid fruit that are firm with a 60-80% red blush over a light yellow-green ground color, and suitable for fresh market use.

4 Drawing Sheets

Latin name of the genus and species of the plant claimed: *Prunus persica.*

Variety denomination: 'TRH2E120LW'.

CROSS-REFERENCE TO RELATED APPLICATIONS

Peach trees developed under the same breeding program as 'TRH2E120LW' include the co-pending applications listed below.

| U.S. application Ser. No. | Title |
|---|---|
| U.S. 19/336,141 | PEACH TREE NAMED 'TX3C490LWP' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,365 | PEACH TREE NAMED 'TRH3C113LW' |
| U.S. 19/336,368 | PEACH TREE NAMED 'TRH3E88LW' |
| U.S. 19/336,370 | PEACH TREE NAMED 'TX2B449LW' |
| U.S. 19/336,372 | PEACH TREE NAMED 'TX2C465CW' |
| U.S. 19/336,375 | PEACH TREE NAMED 'TX2C465CW' |
| U.S. 19/336,377 | PEACH TREE NAMED 'TRH3C111' |
| U.S. 19/336,380 | PEACH TREE NAMED 'TRH2C108W' |

-continued

| U.S. application Ser. No. | Title |
|---|---|
| U.S. 19/336,383 | PEACH TREE NAMED 'TRH2E116L' |
| U.S. 19/336,385 | PEACH TREE NAMED 'TRH2B102LW' |

BACKGROUND OF THE INVENTION

This invention relates to a peach tree and, more specifically, to a peach tree referred to as a variety of *Prunus persica* named 'TRH2E120LW', which requires approximately 250 chilling units of dormancy and produces a firm clingstone to semi-freestone, white-fleshed, subacid peach with a 60-80% red blush over a light yellow-green ground color that matures early mid-season. The present peach tree was the result of an ongoing Stone Fruit Breeding Program in College Station, Brazos County, Texas. To this end, controlled crosses were made each year to produce seedling populations from which improved progenies are evaluated and selected. The seedling 'TRH2E120LW' was derived from a population of seedlings from the open pollination of the white-fleshed peach selection 'TX3E405W' (not patented). Given the subacid nature of the low chill 'TRH2E120LW' the unknown pollen parent was a low-chill, subacid selection. 'TX3E405W' was selected from a progeny created by crossing the low-chill, white-fleshed selection 'TX1B178W' (not patented) with the pollen of the yellow-fleshed nectarine 'Smooth Texan Two' (Byrne, D. H. and N. Anderson. 2014. Smooth Texan nectarines, Three medium chill, early season yellow cultivars. HortScience 49 (8): 1095-1096. Patent, U.S. Plant Pat. No. 28,360, 5 Sep. 2017). TX1B178W was selected from a progeny created from a cross between 'Flordaglo' (Sherman, W. B. and P. M. Lyrene. 1989. Flordaglo peach. HortScience 24:396, not patented) and Thai Tiger TXW1193-1 (Byrne, D. H. and U. Boonprakob. 2008. Thai Tiger low chill peach series. HortScience 43:2226-2227, not patented). Resulting seed from the open pollinated population from 'TX3E405W' were planted in 2011 in an experimental plot in Floresville, TX. 'TRH2E120LW' was marked for subsequent observation in 2013 and noted as having exceptional characteristics.

'TRH2E120LW' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year old and older trees in Pleasanton (2018-2019), Somerville (2016-2020) and Fairfield (2015-2020), Texas. This evaluation clearly demonstrated that the re-propagated trees were true to the characteristics of the original seedling in all observable aspects.

SUMMARY OF THE INVENTION

The 'TRH2E120LW' is a low chill peach that is characterized by producing clingstone to semi-freestone, white-fleshed, subacid, firm fruit with a 60-80% red blush over a light yellow-green ground color that ripens in the early mid-season. In this regard, the present variety of peach tree bears fruit that are ripe for commercial harvesting and shipment in early to mid-June, when the fruit is grown in the medium chill zone of Texas. 'TRH2E120LW' blooms 2 weeks before and ripens with its female parent 'TX3E405W' (not patented). 'TRH2E120LW' differs from its white-fleshed, acid, peach female parent as it has subacid flesh and requires 300 chill hours less to fruit. This new subacid, white-fleshed peach exhibits potential to be commercialized in regions that have chilling requirements that are very low.

'TRH2E120LW' differs from the commercial subacid, white-fleshed peach cultivars 'White Delight One' (not patented, U.S. Plant patent application Ser. No. 14/544,514, USPP Pub. No. 2016/0205833 P1) and 'White Delight Two' (not patented, U.S. Plant patent application Ser. No. 14/544,507, USPP Pub. No. 2016/0205832 P1, abandoned) as it has showy flowers versus non showy flowers, has reniform glands versus globose glands, requires 300 fewer chilling hours to fruit normally, blooms about 3 weeks earlier and ripens later (12 June versus 5 May and 6 June) than 'White Delight One' and 'White Delight Two'.

BRIEF DESCRIPTION OF THE DRAWINGS

This new variety of peach tree is illustrated by the accompanying photographs of 3-year old plants grown in Somerville, Texas, as provided in FIGS. 1-4. These photographs show the plant's typical fruit, foliage, and flowers, and the colors shown are as true as can be reasonably obtained by conventional photographic procedures.

DETAILED BOTANICAL DESCRIPTION

Figure 1:
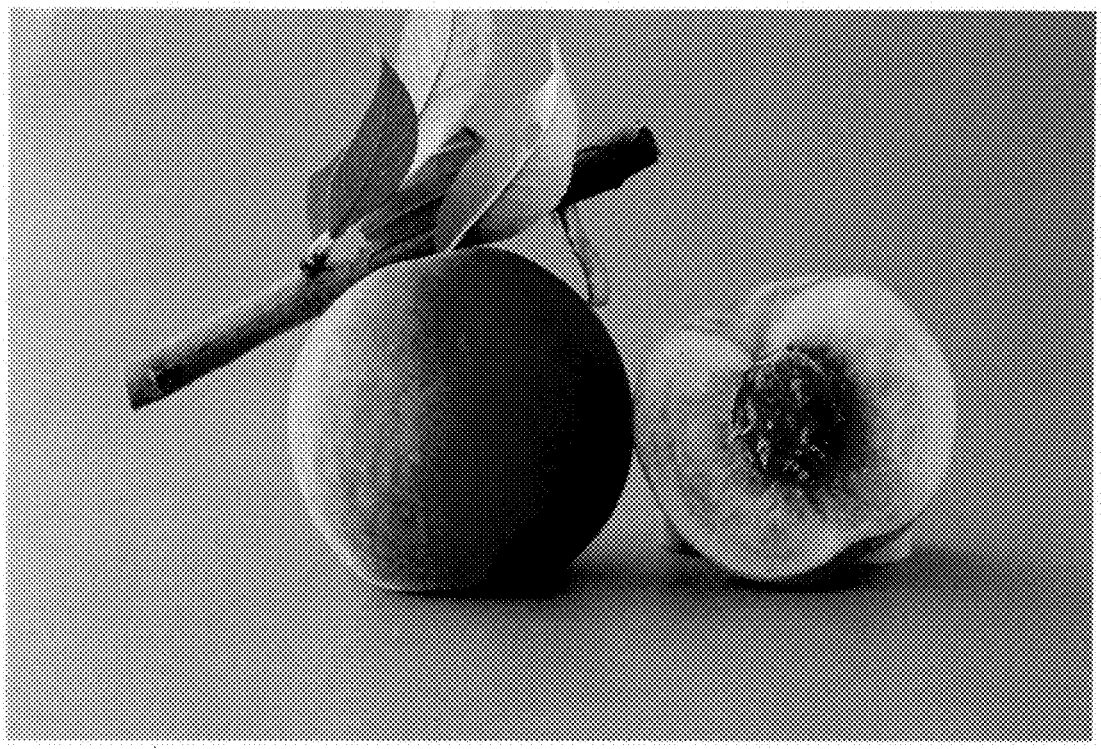
FIG. 1. Fruit of 'TRH2E120LW' produced in Somerville, Texas showing external and internal coloration.
Figure 2:
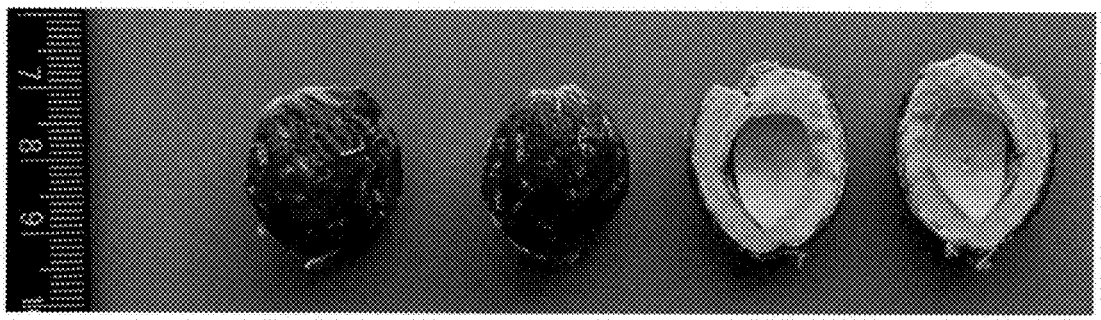
FIG. 2. Photograph of the endocarps of 'TRH2E120LW' peach. The ruler is in centimeters.
Figure 3:
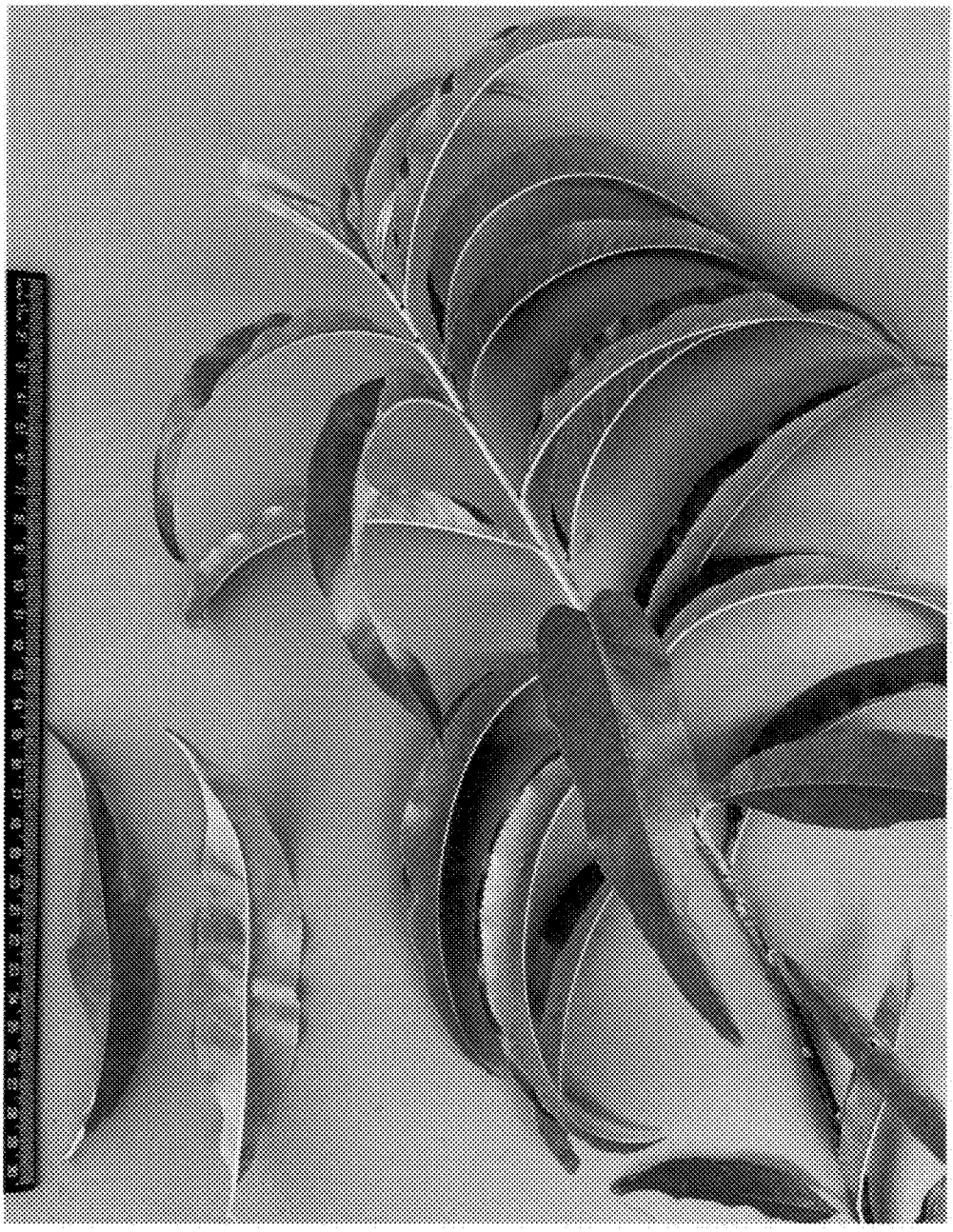
FIG. 3. A stem showing the leaves of 'TRH2E120LW' peach. The ruler is in centimeters.
Figure 4:
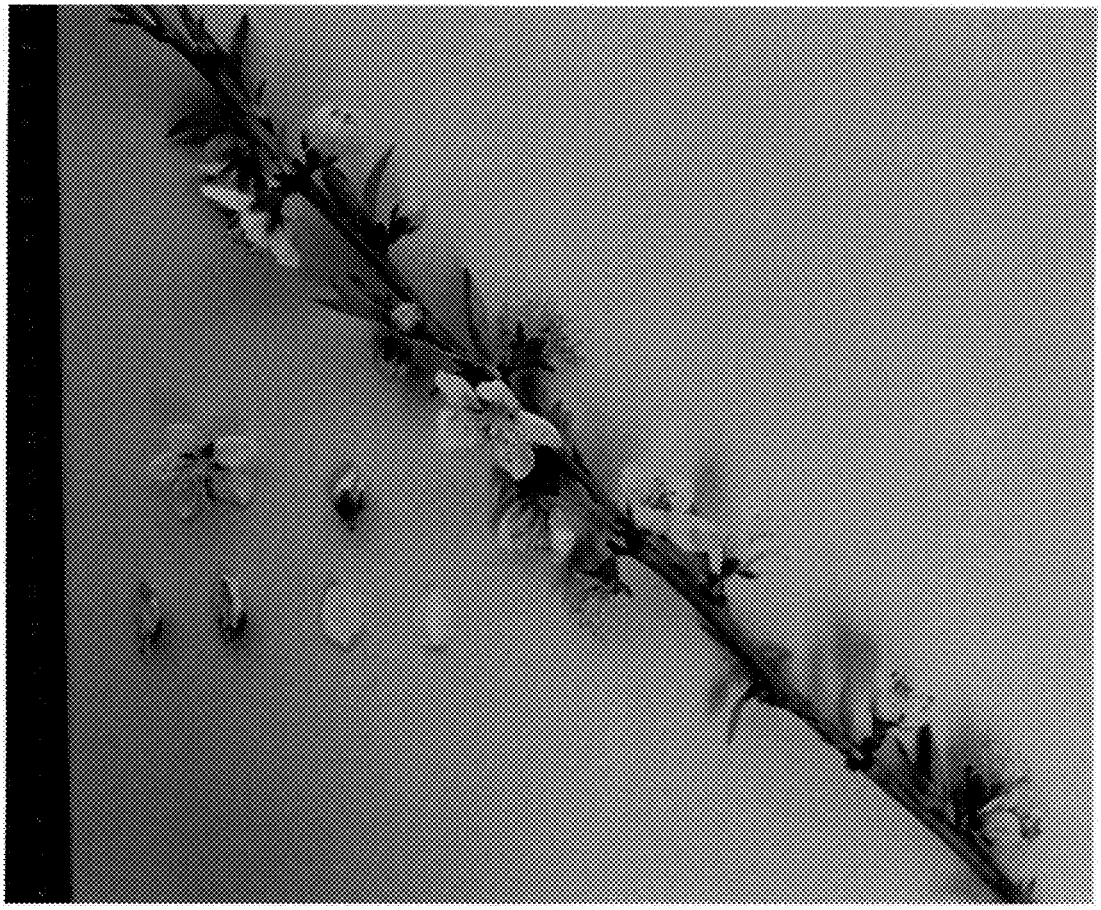
FIG. 4. A stem showing the flowers of 'TRH2E120LW' peach. The ruler is in centimeters.

Referring more specifically to the pomological details of this new and distinct variety of peach tree, the following has been observed under the ecological conditions prevailing at the experimental orchards in the medium chill zone of Texas (Pleasanton, Fairfield and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average as compared to other common peach cultivars grown in the medium chill zone of Texas.

*Height*.—6 to 7 feet (1.8 to 2.1 m) at the end of the 2024 growing season.

*Width*.—7 feet width (2.1 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TRH2E120LW' peach has been trained to an open center configuration but exhibits a semi spreading growth type as seen in peach varieties 'Texprince' (Byrne, D. H. and T. A. Bacon. 2004. TexPrince, a mid-season medium chill peach. HortScience 39(3):631-632; U.S. Plant Pat. No. 14,629, 23 Mar. 2004) and 'Texking' (Byrne, D. H. and T. A. Bacon. 2004. TexKing, an early ripening medium chill peach. HortScience 39:442-443, U.S. Plant Pat. No. 14,627, 23 Mar. 2004).

*Current season growth*.—The current season growth for the new variety was approximately 1 to 2.5 feet (0.3-0.76 m). Vigor is medium to medium low compared to other common peach varieties grown in the medium chill zone of Texas.

*Regularity of bearing*.—Regular in the absence of temperatures of 28° F. or lower and considered hardy in the medium chill zone of Texas.

Trunk:

*Size*.—Approximately 2.25 inches (5.7 cm) in diameter and 8.25 inches (21 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration*.—Variable, colors (RHS2001) present are 156C and 156D of the Greyed-White Group, 163A, N163B, 164A, 165B, 165C, 166A, 176A and 176B of the Greyed-Orange Group, N200D of the Brown Group and 201D of the Grey Group.

Branches:

*Thickness*.—About 2.7 to 4.0 cm in diameter as measured 10 cm from the trunk on a three-year old tree.

*Surface texture*.—Average and appearing furrowed on wood that is several years old.

*Lenticels*.—Numerous flat, oval lenticels present. The lenticels range in size from approximately 2 to 5 mm in width and were approximately 1 to 2 mm in height.

*Current season shoots*.—Surface texture — Substantially glabrous.

*Internode length*.—Approximately 19 to 23 mm as measured in the middle of a current season stem.

*Color of mature branches*.—The predominant colors (RHS2001) are 163A, 164A, 165B and 166A of the Greyed-Orange Group and 201D of the Grey Group.

*Current season shoots*.—Color (RHS2001)-Light to medium green (144A and 144B of Yellow-Green Group) with some reddish-brown coloration appearing on exposed surface of the shoots (178A of the Greyed-Red Group and 183A, 183B, 183C, 185A and 187B of the Greyed-Purple Group).

Leaves:

*Size*.—Considered moderately small for the species. Leaf measurements have been taken from vigorous upright current season growth approximately at mid-shoot.

*Leaf length*.—Approximately 126 to 133 mm.

*Leaf width*.—Approximately 28 to 31 mm.

*Leaf thickness*.—Less than 1 mm.

*Leaf form*.—Lanceolate.

*Leaf tip form*.—Acuminate.

*Leaf upper surface color* (*RHS*2001).—Green, 137B and 137C of the Green Group.

*Leaf lower surface color* (*RHS*2001).—Green, 146A and 146B of the Yellow-Green Group.

*Leaf lower mid-vein color* (*RHS*2001).—Light yellow green, 148D of the Yellow-Green Group.

*Leaf margins*.—Form — Considered crenate. Uniformity — Considered generally uniform.

*Leaf petioles*.—Length — Approximately 8 to 10 mm. Thickness — Approximately 1 to 2 mm. Color — Pale green (N144A, 145A and 151A of the Yellow-Green Group).

*Leaf glands*.—Size — Approximately 1 mm in height and less than 1 mm in width. Number — Generally 0-2 per leaf. Type — Reniform. Color — Brown (165A, 165B and 166C of the Greyed-Orange Group and 199A, N199C and N199D of the Grey-Brown Group).

*Leaf stipules*.—The stipules are considered to be early deciduous and approximately 6-8 mm long.

*Ratio of wood* (*leaf*) *buds to flowering buds*.—Generally 2 flower buds per vegetative bud.

Flowers:

*Floral buds*.—General — The mature floral buds are considered to be conic in form, and slightly appressed relative to the bearing shoot. Color (RHS2001) — The mature buds are medium brown with grey (approximately 156A, 156B, 156C and 156D of the Greyed-White Group, 157A, 157B, 157C and 157D of the Green-White Group, 165A, 166A, 166B, 175A, 177A and 177B of the Greyed-Orange Group, 183B of the Greyed-Purple, 197A and 197B of the Greyed-Green Group, 199A, N199A, N199B and N199C of the Grey-Brown Group and 200C of the Brown Group). The buds are considered hardy in the medium chill zone of Texas. Mature Bud Length — 5 to 6 mm. Mature Bud Width — 1 to 2 mm.

*Blooming type*.—Considered very early in relation to other peach cultivars commonly growing in the medium chill zone of Texas. The average date of full bloom was February 6$^{th}$ in Somerville during the period of 2016-2023. This is 3 days after the low chill peach 'TexFirst' (Byrne, D. H. and N. Anderson. 2012. 'TexFirst', An early ripening low chill peach for the subtropics. HortScience 47:1803-1804. U.S. Plant Pat. No. 26,199, 24 Nov. 2015) and 11-16 days before the medium chill peaches 'Flordaking' (not patented, Andrews, 1979) and 'TexKing'. The chilling requirement of TRH2E20LW is estimated to be about 250 chill hours.

*Flower type*.—Showy.

*Flower size*.—Flower diameter at full bloom is approximately 38 to 41 mm.

*Bloom quantity*.—Considered abundant.

*Flower bud frequency*.—Normally 1 to 2 per node.

*Petal size*.—Width — Approximately 9 to 10 mm. Length — Approximately 17 to 19 mm.

*Petal form*.—Broadly ovate

*Petal number*.—Nearly always 5.

*Petal abaxial/adaxial color* (*RHS*2001).—Light pink when young (62D, 65C, 65D, 69A, 69B, 69C and 73D of the Red-Purple Group and 75D of the Purple Group), becoming darker with advanced senescence.

*Petal claw*.—Form — The claw is considered truncate in shape. Length — Approximately 1 mm. Width — Approximately 1 mm.

*Petal margins*.—Generally considered variable, from nearly smooth to slightly undulate.

*Petal apex*.—Generally — The petal apices appear round.

*Flower pedicel*.—Length — Considered medium, and having an average length of approximately 2 to 3 mm. Thickness — Approximately 1 to 2 mm. Color (RHS2001) — Light green (144D, N144D and 145A of the Yellow-Green Group).

*Floral nectaries*.—Color — Variable, medium yellow to medium orange (13A, 13B and 13C of the Yellow Group and 15B, 15C, 15D, 17B, 21A and 23B of the Yellow-Orange Group and 25A, 25B, N25A, N25B, N25C and 28B of the Orange Group).

*Sepals*.—Surface Texture — The surface has a short, fine, wooly texture. Size — Average Height 6.3 mm; Width 4.5 mm. Sepal Form — Ovate. Sepal Number — Generally five per flower. Color (RHS2001) — Green and maroon with white (approximately 58A, 59B, 60A and 60B of the Red-Purple Group; 144C, 144D, N144D, 145A and 145B of the Yellow-Green Group and 155A, 155B, 155C and 155D of the White Group).

*Floral cup* (*hypanthium*).—Surface Texture — Generally glabrous. Color (RHS2001) — Green with maroon (approximately 58A, 59B, 60A and 60B of the Red-Purple Group and 144C, 144D, N144D, 145A and 145B of the Yellow-Green Group).

*Anthers*.—Color (RHS2001) — Medium to dark yellow (approximately 6B, 6C, 7C and 7D of the Yellow Group and 14A and 14B of the Yellow-Orange Group).

*Pollen production*.—Pollen is abundant and is a bright medium yellow color (approximately RHS2001 2A, 3A, 3B, 3C, 4A, 5A, 5B, 5C, 6A, 6B, 6C, 7A, 7B, 7C, 7D, 8A, 8B, 9A, 9B and 9C of the Yellow Group).

*Filaments*.—Size — Variable in length, approximately 14 to 16 mm, with the filaments generally equal to or slightly shorter than the pistil and slightly below the petal height. Color (RHS2001) — White (approximately 155A and 155B of the White Group) and darkening with advanced maturity.

*Pistil*.—General — Pistil is equal to or slightly taller than the anther height and generally slightly below the petal height. Length — Approximately 13 to 19 mm, including the ovary. Color (RHS2011) — Considered white with yellow when young (approximately 1A, 1B, 1C and 1D of the Green-Yellow Group; 155A, 155B, 155C and 155D of the White Group and 158A, 158B, 158C and 158D of the Yellow-White Group) and becoming slightly darker with advancing senescence.

*Surface texture*.—The variety has a short, silver white pubescent pistil (approximately RHS2001 155A, 155B, 155C and 155D of the White Group).

Fruit:

*Maturity when described*.—The present variety of fruit is described, as it would be found in its firm ripe condition at full commercial maturity. Under the ecological conditions prevailing in the medium chill zone of Texas it would be ripe in early to mid-June. The average ripe date was June 5$^{th}$, June 12$^{th}$ and June 3$^{rd}$ in Pleasanton, Somerville, and Fairfield respectively.

*Size*.—General — Medium large to large for the season and considered uniform. Average Cheek Diameter — Approximately 58 to 64 mm. Average Suture Diameter — Approximately 60 to 66 mm. Average Axial Diameter — Approximately 48 to 56 mm.

*Fruit form*.—Generally considered oblate. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Dark pink, 59B, 59C. 60A and 60B of the Red-Purple Group.

*Ventral surface*.—Form-Considered uniform.

*Stem cavity*.—Width — Approximately 13 to 18 mm. Length — Approximately 20 to 24 mm. Depth — Approximately 11 to 12 mm.

*Fruit base*.—Round and flat.

*Fruit apex*.—Flat.

*Fruit stem*.—Length — 9 to 12 mm. Thickness — Approximately 2 mm. Color (RHS2001) — Light to medium green, 144B, N144D, 145A, 145B and 145C of the Yellow-Green Group.

*Fruit skin*.—Generally considered medium or average in thickness. Surface Texture — Light in color with medium pubescence. Skin Acidity — Considered neutral. Tenacious to Flesh — Yes at commercial maturity. Tendency to Crack — No cracking observed. Skin Color (RHS2001) — Generally — Variable, with approximately 60-80% of the fruit surface covered with a red blush. Blush Color (RHS2001) — Marbled to solid pink to dark red, 46A, 48B, 48C, 49A, 51C and 53A of the Red Group and 59A and 59B of the Red-Purple Group. Skin Ground Color (RHS2001)-Light yellow green, 1C and 1D of the Green-Yellow Group, and 2C and 2D of the Yellow Group.

*Flesh color* (*RHS*2001).—White, 155A, 155B, 155C and 155D of the White Group. Anthocyanin coloration of the flesh is generally weak to medium next to the skin, centrally and next to the pit.

*Flesh fibers*.—Present throughout the flesh.

*Stone cavity color* (*RHS*2001).—White with dark red, 155A, 155B, 155C and 155D of the White Group, 46A and 53A of the Red Group and 59B, 59C, 60A and 60B of the Red-Purple Group.

*Flesh texture*.—Generally, the flesh is considered firm at commercial maturity.

*Ripening*.—Generally the fruit of the present variety ripens evenly.

*Flavor*.—Considered very sweet (average Brix 14.3) and rich subacid flavor.

Stone:

*Attachment*.—Clingstone to semi freestone at commercial maturity.

*Stone size*.—Generally considered medium relative to the ratio of stone to fruit size. Length — Approximately 24 to 29 mm. Width — Approximately 20 to 23 mm. Thickness — Approximately 15 to 17 mm.

*Fibers*.—Generally a few fibers are attached sporadically along the surface of the stone.

*Stone form*.—Rounded.

*Stone base*.—Wide.

*Stone apex angle*.—Medium to wide.

*Stone shape*.—Considered ovoid.

*Stone surface*.—Surface Texture — Consists of single pits and rosettes of pits. Ridges — Numerous fine ridges are present basally and converge towards the base of the stone.

*Ventral edge*.—Medium.

*Dorsal edge*.—Shape — Grooved and having moderately rough edges.

*Stone color* (*RHS*2001).—The color of the dry stone is medium brown with dark pink, 59A and 59B of the Red-Purple Group, N77A of the Purple Group, 164B, 164C, 165B and 165C of the Greyed-Orange Group and 186C, 186D, 187A, 187B and 187C of the Greyed-Purple Group. The color of the inside surface of the endocarp is primarily tan, 158A of the Yellow-White Group and 164C, 164D and 165D of the Greyed-Orange Group.

*Tendency to split*.—Splitting is relatively uncommon.

*Kernel*.—The kernel fills the endocarp at harvest and measures approximately 6 mm in thickness, 10-11 mm in width, and 13-17 mm in length. The colors (RHS2001) of the fresh kernel are pale yellow, 4D, 5D, 8C, 8D, 10D, 11C, 11D, 12D and 13D of the Yellow Group and 14D, 18C and 18D of the Yellow-Orange Group. When dried the shriveled kernels measure approximately 4-5 mm in thickness, 9-10 mm in width, and 13-16 mm in length. The colors of the shriveled kernels are primarily tan to light brown, 158A of the Yellow-White Group, 161A and 161B of the Greyed-Yellow Group and 164B, 164C, 165C and 165D of the Greyed-Orange Group.

*Use*.—The subject variety, 'TRH2E120LW', is considered to be a low chill peach tree of early mid-season maturity, which produces subacid, white-fleshed fruit which are firm with a 60-80% red blush over a light yellow-green ground cover, and which are useful for the fresh fruit market.

*Keeping quality*.—Average. Retains firmness and flavor after 14 days of refrigeration at 3-5° C.

*Resistance to insects and disease*.—No atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Pleasanton, Somerville and Fairfield, it will be understood that variations of the usual magnitude and characteristics incident to the changes in growing conditions, fertilization, pruning, and pest control are to be expected.

What is claimed is:

1. A new and distinct variety of peach tree named 'TRH2E120LW', as illustrated and described herein.

* * * * *